United States Patent [19]

Patel et al.

[11] Patent Number: 5,756,124
[45] Date of Patent: May 26, 1998

[54] MULTI-SCORED PHARMACEUTICAL TABLETS

[75] Inventors: Mahendra R. Patel; Rajendra Patel, both of East Brunswick, N.J.

[73] Assignee: Invamed, Inc., Dayton, N.J.

[21] Appl. No.: 694,794

[22] Filed: Aug. 9, 1996

Related U.S. Application Data

[63] Continuation of Ser. No. 512,168, Aug. 7, 1995, abandoned.

[51] Int. Cl.⁶ ............................................. A61K 9/44
[52] U.S. Cl. ............................ 424/467; 424/464; 424/474
[58] Field of Search ............................... 424/464, 465, 424/467

[56] References Cited

U.S. PATENT DOCUMENTS

| | | | |
|---|---|---|---|
| D. 89,941 | 7/1933 | Low | 424/467 |
| D. 216,307 | 12/1969 | Ninger | D16/3 |
| D. 229,049 | 11/1973 | Roberts | D16/3 |
| D. 334,420 | 3/1993 | Gladfather et al. | D23/207 |
| 4,215,104 | 7/1980 | Ullman et al. | 424/15 |
| 4,258,027 | 3/1981 | Ullman et al. | 424/15 |
| 4,353,887 | 10/1982 | Hess et al. | 424/15 |
| 5,520,929 | 5/1996 | Makino et al. | 424/467 |

*Primary Examiner*—Thurman K. Page
*Assistant Examiner*—Sharon Howard
*Attorney, Agent, or Firm*—Plevy & Associates

[57] ABSTRACT

A solid pharmaceutical tablet having a predetermined dosage that can be divided into a plurality of sub-dosage units by applying a minimal amount of force to the tablet. The tablet comprises a solid body having a top surface, a bottom surface, an outer surface, and an inner surface. The inner surface defines an aperture having a shape corresponding to the shape of the tablet. The area of the aperture is at least 15% of the area of the tablet. Impressed within the top surface of the tablet are a first plurality of symmetrical score lines and impressed within the bottom surface of the tablet are a second plurality of symmetrical score lines. The score lines extend from the aperture to the outer surface of the tablet. Finally, each of the sub-dosage units has a dosage that is a fraction of the predetermined dosage of the tablet.

7 Claims, 9 Drawing Sheets

80

90

MULTI-SCORED PHARMACEUTICAL TABLETS

This is a continuation of application Ser. No. 08/512,168, filed on Aug. 7, 1995, entitled MULTI-SCORED PHARMACEUTICAL TABLET and now abandoned.

FIELD OF THE INVENTION

The present invention relates generally to a pharmaceutical tablet, and more particularly, to a pharmaceutical tablet which can be easily divided into a plurality of sub-dosage units.

BACKGROUND OF THE INVENTION

It is well known in the pharmaceutical art that tablets may be formed with a groove or score marking to facilitate breakage of the tablet into sub-dosage units. Typically, these tablets have a transverse score marking disposed along the top surface of the tablet such that the tablet may be severed into half-sections.

Because of the inherent difficulties of breaking a grooved tablet into accurate predetermined dosages, a variety of diverse attempts have been made in the prior art seeking tablet structures which are readily fractured into sub-dosage units by application of moderate manual pressure. For example, U.S. Pat. No. 4,215,104 to Ullman et al. discloses a multi-score rectangular tablet having readily severable sections which may divided to form either bisectional or trisectional sub-dosage units. In addition, U.S. Design Pat. No. 334,420 shows a multi-score chemical detergent block which may be divided to form up to 6 units. None of these patents, however, have provided a multi-score tablet that can be easily divided into a plurality of accurate sub-dosage units.

Inherently, the problem of breaking the grooved tablets of the prior art resides in the hardness factor of the tablet resulting from the compression techniques used to form the tablet. Further, the small size configuration of the tablet does not allow for easy breakage. In fact, a sharp instrument is often required to sever the tablet, which frequently results in fracture of the tablet into undesired miniature pieces of inaccurate dosages. Additionally, the pressure that is required to sever the tablet frequently propels both sections of the tablet, unless extreme care is used to contain the pieces during severance.

Furthermore, such prior art tablets generally offer sub-dosage units having a limited range of dosages. Thus, more expensive multiple tablets are required to compensate for dosages that are not available from prior art grooved tablets.

Accordingly, it is the object of the present invention to substantially overcome or eliminate such disadvantages by providing a multi-scored pharmaceutical tablet of a predetermined dosage having an aperture which allows the tablet to be easily divided into a plurality of sub-dosage units, each having a dosage that is a fraction of the predetermined dosage.

SUMMARY OF THE INVENTION

The present invention is a scored pharmaceutical tablet having a predetermined dosage which can be divided into a plurality of sub-dosage units by applying a minimal amount of force to the tablet. The Multi-Scored Pharmaceutical Tablet comprises a solid body, a top surface, a bottom surface, an outer surface and an inner surface. The inner surface of the tablet defines an aperture that is at least 15% of the area of the tablet. A plurality of score lines are impressed within the top surface of the tablet and within the bottom surface of the tablet, and extend from the inner surface of the tablet to the outer surface of the tablet. The tablet can be severed into a plurality of sub-dosage units, each having a dosage that is a fraction of the predetermined dosage of the tablet.

BRIEF DESCRIPTION OF THE DRAWINGS

The foregoing and other objects, features, and advantages of the invention will be apparent from the following more particular description of the preferred embodiments of the invention, as illustrated in the accompanying drawings, wherein.

DETAILED DESCRIPTION OF THE INVENTION

Figure 1:
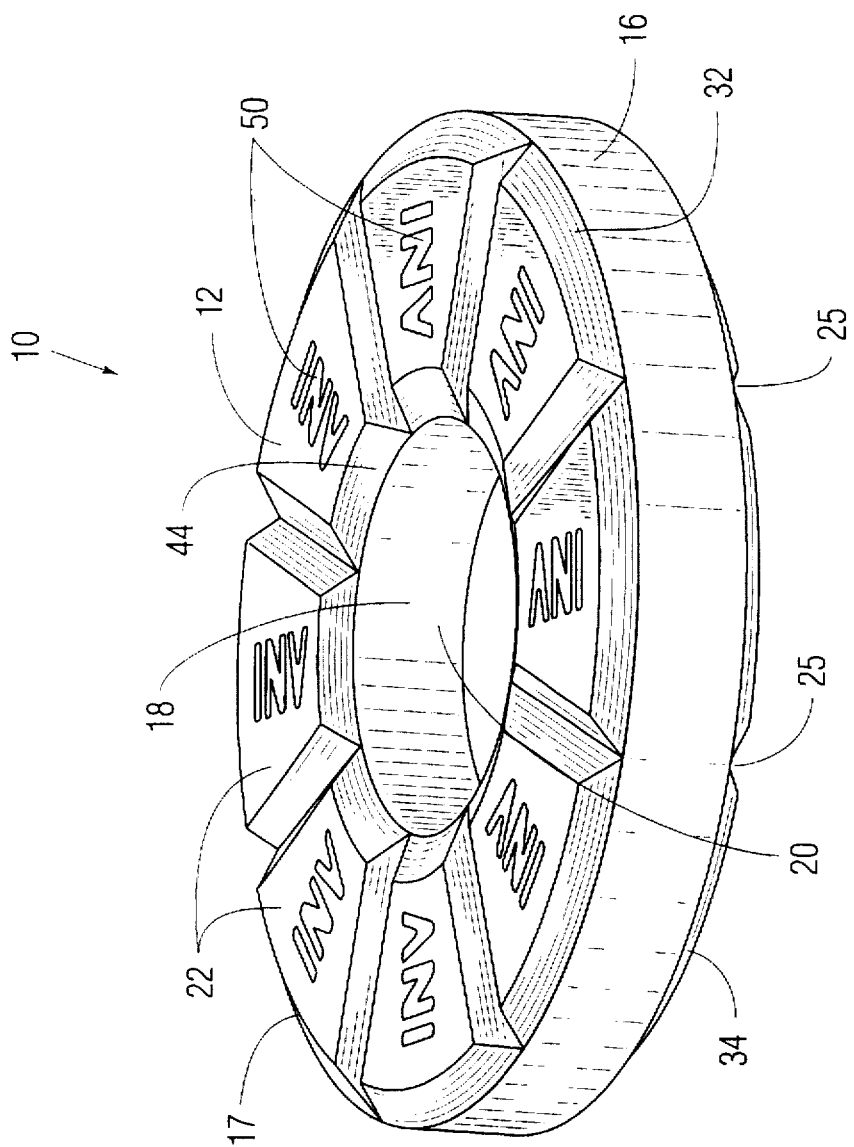
FIG. 1 is a perspective view of an exemplary embodiment of the present invention.
Figure 2:
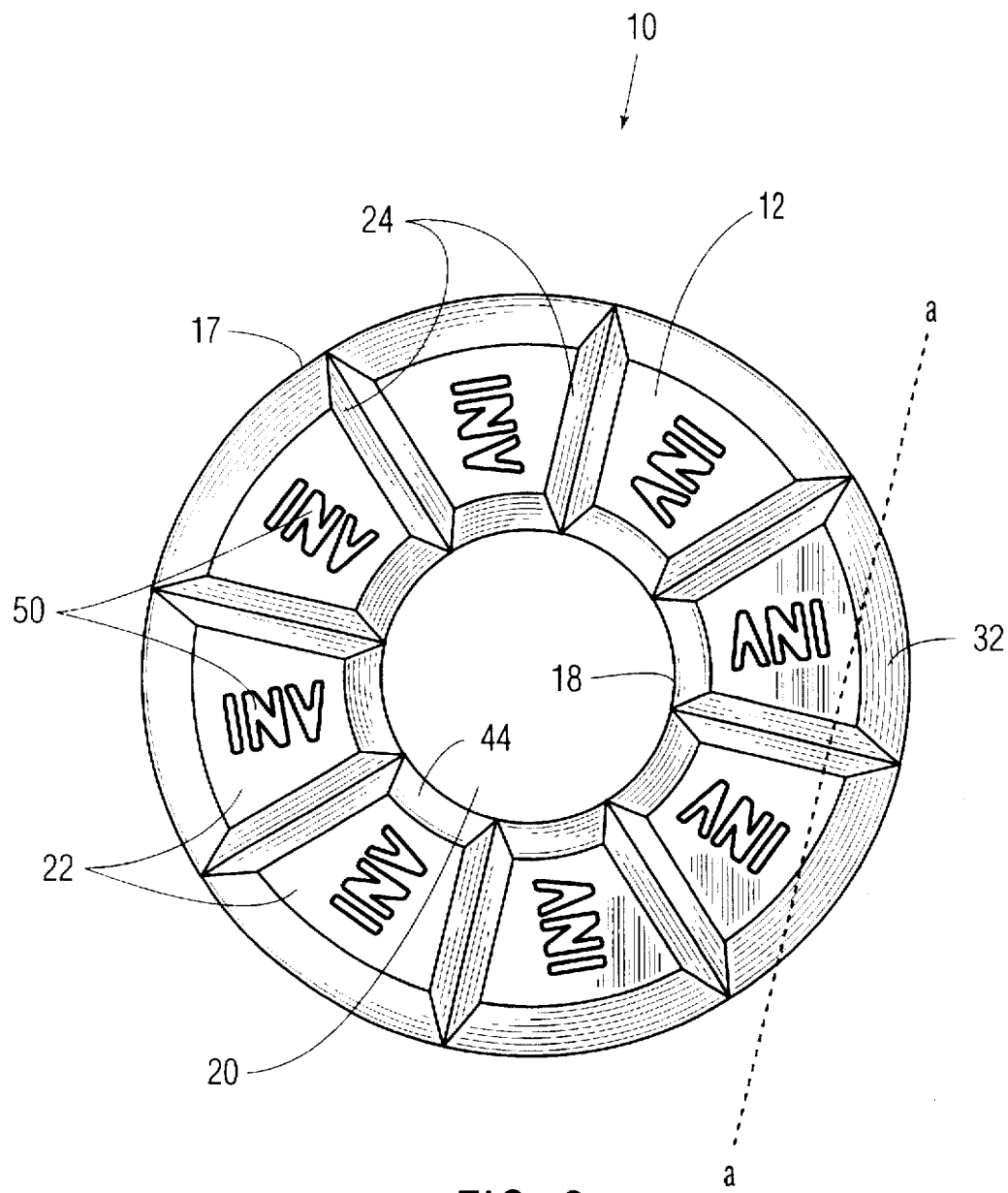
FIG. 2 is a top view of the exemplary embodiment of the tablet shown in FIG. 1.
Figure 3:
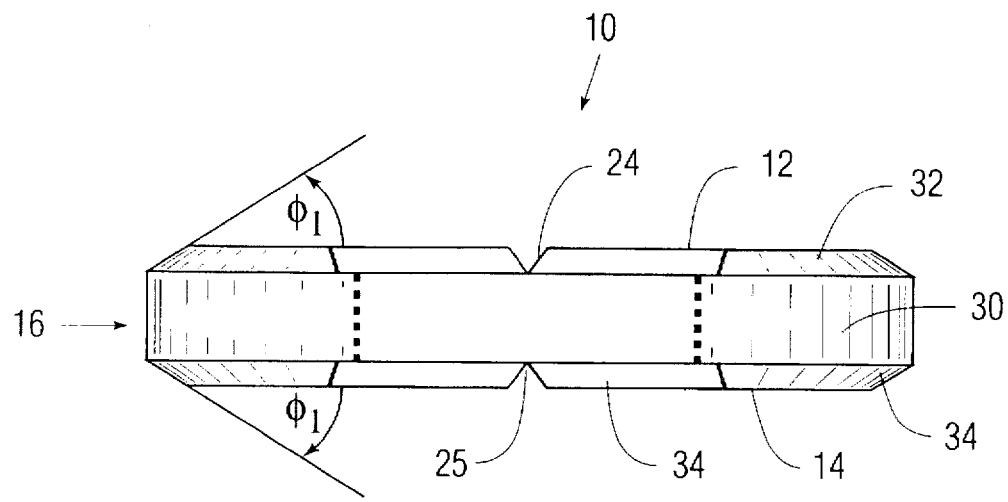
FIG. 3 is a front view of the exemplary embodiment of the tablet shown in FIG. 1.

The present invention is directed to a pharmaceutical tablet that can be severed into a given number of sub-dosage units. The tablet of the present invention comprises a solid body and is formed using compression techniques that are well known in the prior art. Referring to FIGS. 1–3, the tablet of the present invention 10 is generally toroidal, comprising a top surface 12, a bottom surface 14, and an outer surface 16 defining an outer periphery 17. An annular inner surface 18 defines an aperture 20 which extends between the top 12 and bottom 14 surfaces. It should be understood that the outer 16 and inner 18 surfaces of the present invention 10 are not limited to the shape of the exemplary embodiment tablet shown in FIGS. 1–3 and can comprise other shapes such as octagonal, oval, etc.

Referring to FIGS. 1 and 2, the top surface 12 and bottom surface 14 of the tablet 10 duplicate each other with the top surface 12 being divided into a first plurality of horizontal planar surfaces 22 by a first plurality of score lines 24. Similarly, the bottom surface 14 of the tablet 10 is divided into a second plurality of horizontal planar surfaces (not shown) by a second plurality of score lines 25.

Referring to FIG. 3, a top outer bevel edge 32 is disposed at the junction of the top of the outer surface 16 and the top surface 12. Similarly, a bottom outer bevel edge 34 is disposed at the junction of the bottom of the outer surface 16 and the bottom surface 14. The top outer bevel edge 32 and the bottom outer bevel edge 34 have a preferred angle of inclination $\theta_1$ of approximately 30°, as measured from the top 12 and bottom 14 surfaces of the tablet 10. This angle optimizes severance of the tablet along the score lines. It should be understood, however, that the angle $\theta_1$ of the outer bevel edges 32 34 can include other angles.

Referring to FIGS. 1 and 2, a top inner bevel edge 44 is disposed at the junction of the top of the inner surface 18 and the top surface 12. In addition, a bottom inner bevel edge 46 is disposed at the junction of the bottom of the inner surface 18 and the bottom surface 14. The top inner bevel edge 44 and the bottom inner bevel edge (not shown) have a preferred angle of inclination $\theta_1$ of approximately 30°, as measured from the top 12 and bottom 14 surfaces of the tablet 10. It should be understood, however, that the angle $\theta_1$, of the inner bevel edges 44 (bottom inner bevel edge not shown) can include other angles.

FIGS. 1-3 show the tablet 10 having eight (8) score lines 24 impressed within the top surface 12 of the tablet 10 and eight (8) score lines 25 impressed within the bottom surface 14 of the tablet 10. It should be understood that the number of score lines 24 25 can be varied providing that the scoring pattern of the top surface 12 of the tablet 10 duplicates the scoring pattern of the bottom surface 14 of the tablet 10.

Each of the first plurality of score lines 24 on the top surface 12 of the tablet 10 extend from the aperture 18 to the outer periphery 17 of the tablet 10. Likewise, each of the second plurality of score lines 25 on the bottom surface 14 of the tablet 10 extend from the aperture 18 to the outer periphery 17 of the tablet 10. Further, the score lines 25 on the bottom surface 14 of the tablet 10 are located directly below the score lines 24 on the top surface 12 of the tablet 10, which facilitates severance of the tablet 10 into a plurality of sub-dosage units 60 70 80 90 100 110 120, as shown in FIGS. 5-12, respectively.

Figure 4:
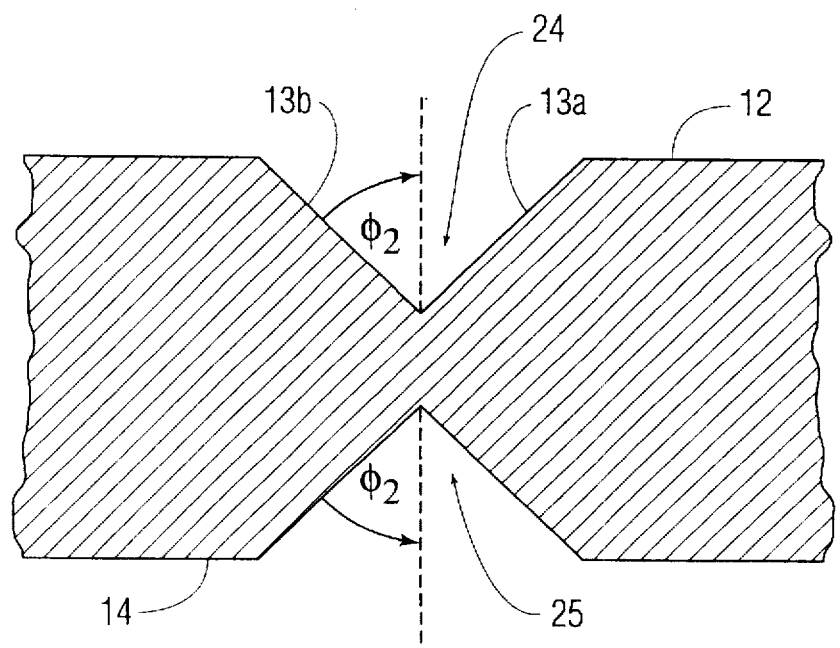
FIG. 4 is a cross-sectional view of the V-shaped score lines shown in FIG. 2 along line a—a.

The score lines 24 25 have a V-shaped cross-section as shown in FIG. 4. Each arm 13a 13b of the score line 24 25 is disposed at an angle $\theta_2$ of preferably about 90° from each other. It should be understood that the angle $\theta_2$ of the arms 13a 13b of the score lines 24 25 can be varied. Further, other suitable score line configurations known in the art can be substituted for the shape of the score lines described above.

Referring to FIGS. 1 and 2, indicia 50 is engraved into the top surface 12 and into the bottom surface 14 of the tablet 10 (the indicia of the bottom surface is not shown). Each of the plurality of horizontal planar surfaces 22 23 of the top surface 12 and of the bottom surface 14 of the tablet 10 are identically marked with the indicia 50. Upon severance of the tablet 10, the indicia 50 can be seen on all of the sub-dosage units, (60 70 80 90 100 110 120 of FIGS. 5-12) and therefore the drug can be identified. Further, the dosages of the sub-dosage units can be ascertained.

The indicia 50 shown in FIGS. 1 and 2 includes a plurality of corporate logos engraved into the top surface 12 and into the bottom surface 14 of the tablet 10. However, the indicia 50 may be varied to indicate dosage or another design.

In addition to the ornamentation described herein, the tablet 10 can be colored as desired to reflect particular dosage units, or may be coated with suitable materials that are well known in the art.

The preferred dimensions of the exemplary embodiment 10 of the present invention include a diameter of approximately 0.4687 inches, a center aperture 20 having a diameter of approximately 0.1875 inches, and a thickness of approximately 0.230 inches. The top outer bevel surface 32, the bottom outer bevel surface 34, the top inner bevel surface 44, and the bottom inner bevel surface (not shown) have depths of approximately 0.0160 inches. Each of the V-shaped score lines 24 have a depth of approximately 0.0150 inches and a width of 0.0320 inches.

The above dimensions can be modified, bearing in mind that modifications to the dimensions of the tablet 10 will affect the severability of the tablet 10. For example, the area of the aperture 20 relative to the area of the tablet 10 affects the force needed to sever the tablet 10. Likewise, the size of the aperture 20 affects the stress incurred in the tablet 10 during severance. Accordingly, the area of the aperture 20 of the tablet should equal at least 15% of the area of the tablet 10.

Further, since the depth of the V-shaped score lines 24 affect the severability of the tablet 10, it is preferable that the depth of each of the score lines 24 remain at least approximately 5% of the thickness of the tablet 10.

By providing the multi-scored tablet 10 of the present invention, the consumer of the tablet can economically and accurately regulate his dosages. For example, the exemplary embodiment of the present invention can be administered as a unitary dosage. Alternatively, the exemplary embodiment can be administered in sub-dosages of ⅛, ¼, ⅜, ½, ⅝, ¾ or ⅞ of the total dosage of the tablet 10, as shown in FIGS. 5-12.

In the event that half a dosage is desired, the tablet 10 may be fractured conveniently along any two score lines 24 along the same linear path on the top surface 12 of the tablet 10 and along the two score lines (not shown) on the bottom surface 14 of the tablet 10 directly below the two score lines along the top surface 12 of the tablet 10. The resulting half dosage sub-dosage unit 60 is shown in FIGS. 5 and 6.

Figure 5:
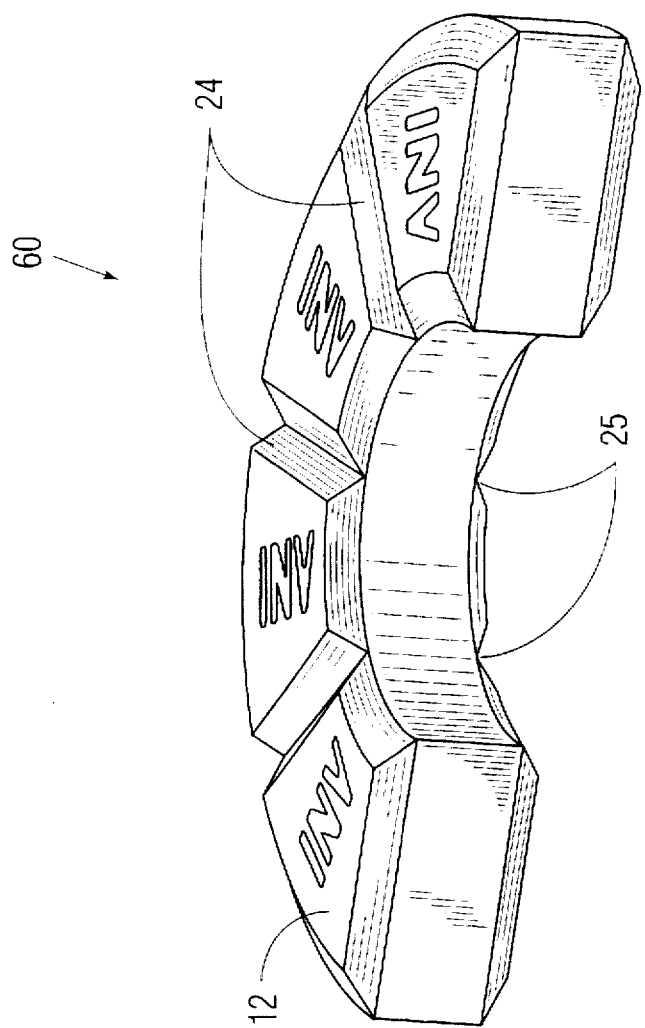
FIG. 5 is a perspective view of a sub-dosage unit of the tablet shown in FIG. 1 having a dosage of ½ of the total dosage of the tablet.
Figure 6:
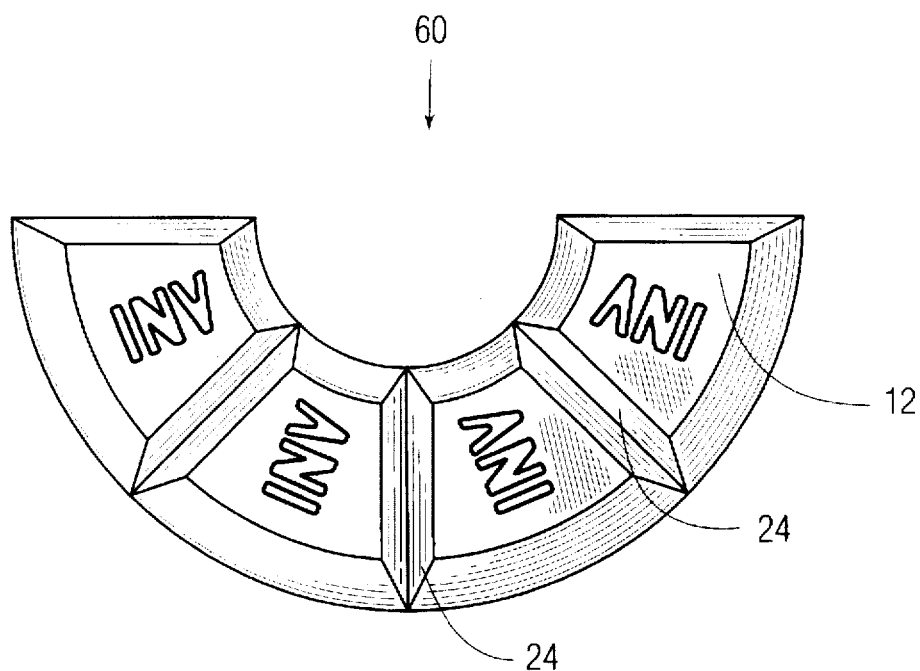
FIG. 6 is a top view of a sub-dosage unit of the tablet shown in FIG. 1 having a dosage of ½ of the total dosage of the tablet.
Figure 7:
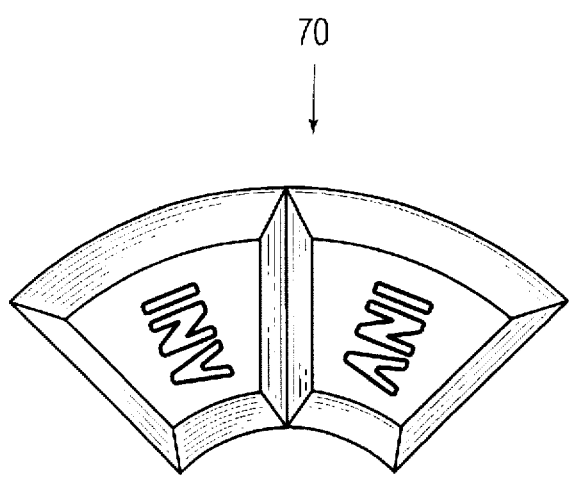
FIG. 7 is a top view of a sub-dosage unit of the tablet shown in FIG. 1 having a dosage of ¼ of the total dosage of the tablet.

In the event that a quarter dosage is desired, the sub-dosage unit 60 shown in FIGS. 5 and 6 can be further severed in half to form the sub-dosage unit 70 shown in FIG. 7.

Figure 8:
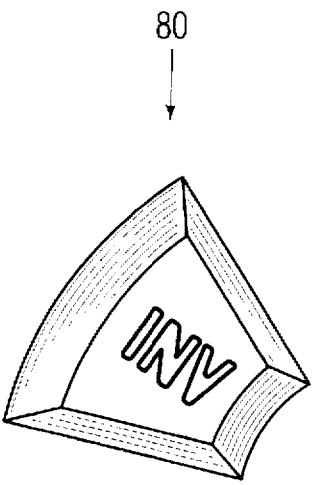
FIG. 8 is a top view of a sub-dosage unit of the tablet shown in FIG. 1 having a dosage of ⅛ of the total dosage of the tablet.
Figure 9:
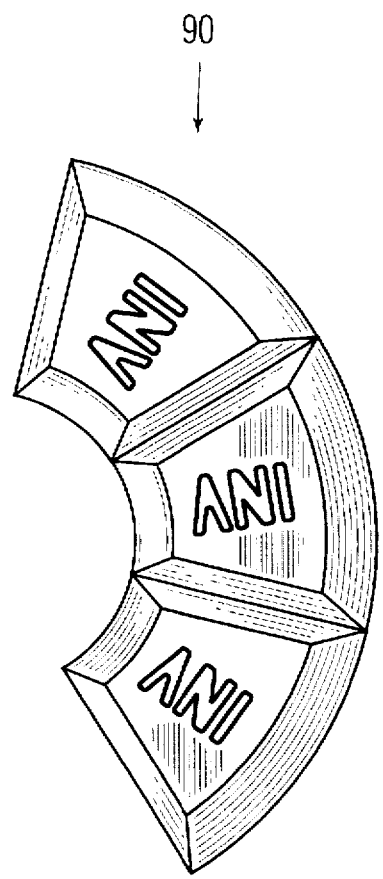
FIG. 9 is a top view of a sub-dosage unit of the tablet shown in FIG. 1 having a dosage of ⅜ of the total dosage of the tablet.
Figure 10:
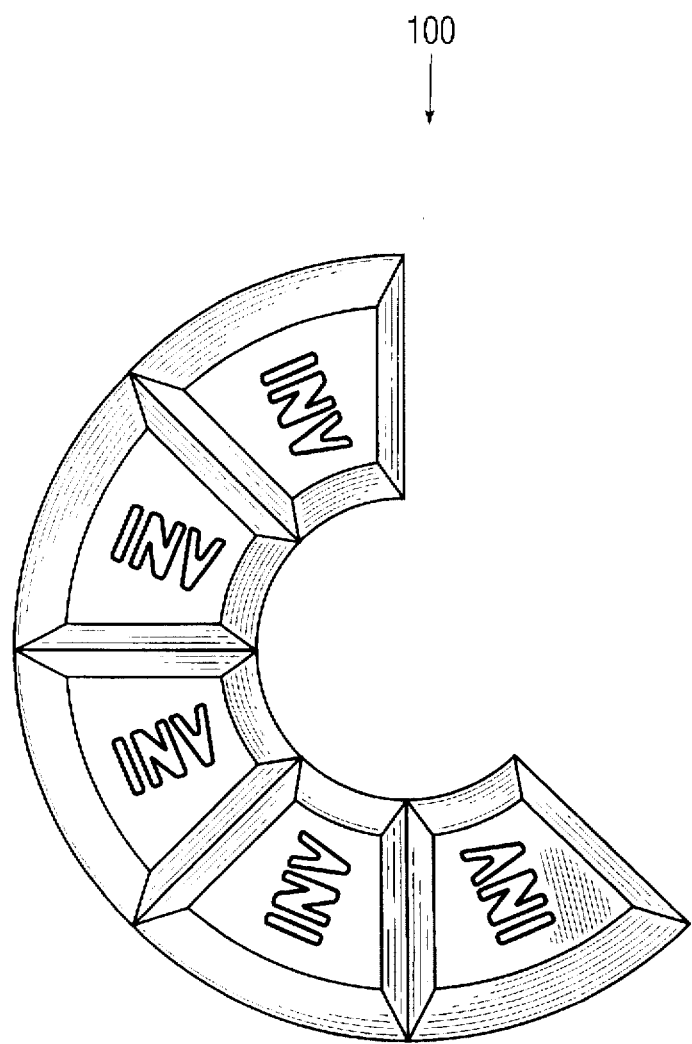
FIG. 10 is a top view of a sub-dosage unit of the tablet shown in FIG. 1 having a dosage of ⅝ of the total dosage of the tablet.
Figure 11:
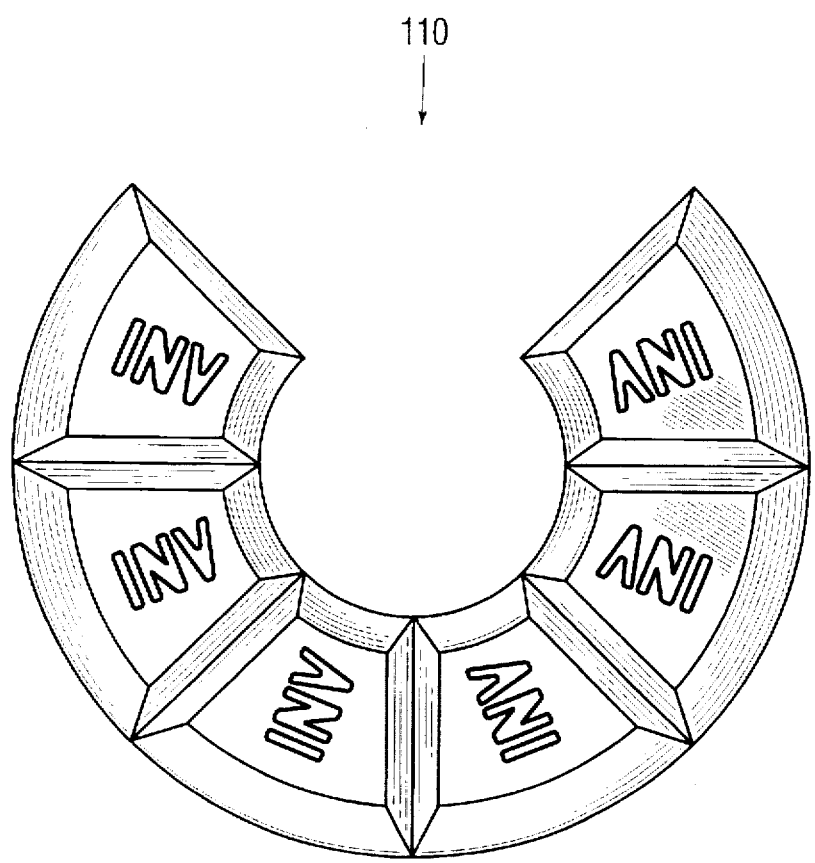
FIG. 11 is a top view of a sub-dosage unit of the tablet shown in FIG. 1 having a dosage of ¾ of the total dosage of the tablet.
Figure 12:
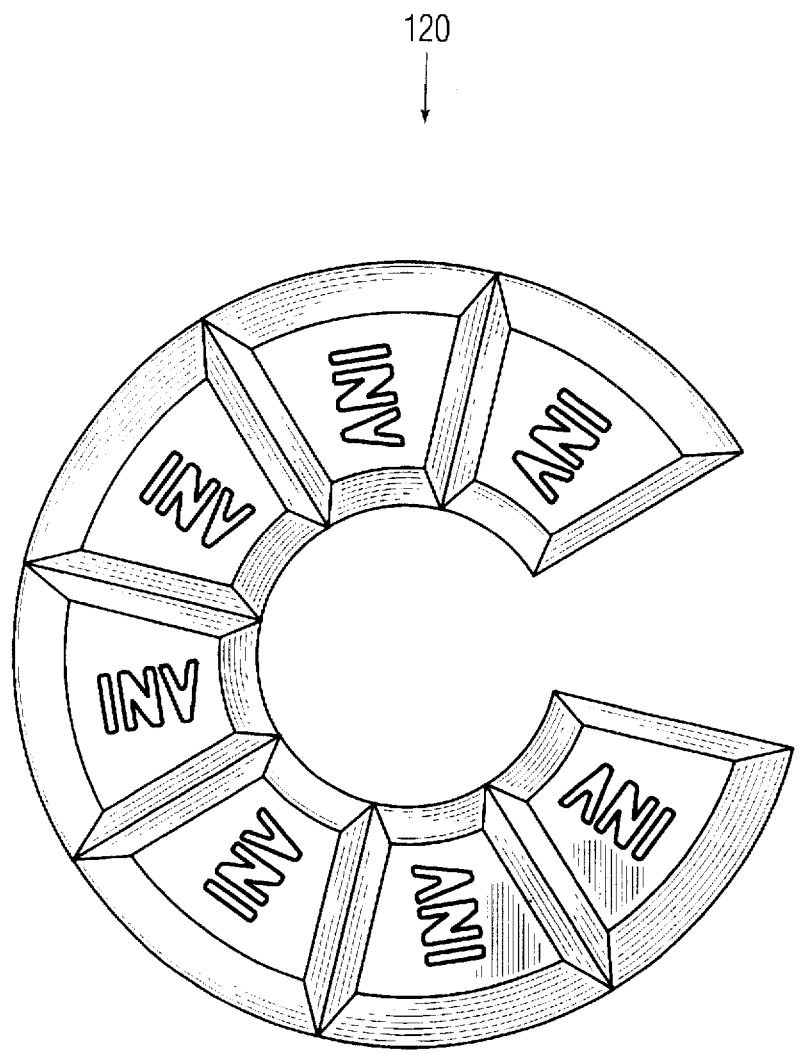
FIG. 12 is a top view of a sub-dosage unit of the tablet shown in FIG. 1 having a dosage of ⅞ of the total dosage of the tablet.

If a dosage of ⅛ of the dosage of the total tablet 10 is desired, the sub-dosage unit 70 shown in FIG. 7 can be severed in half to form the sub-dosage unit 80 shown in FIG. 8.

In addition to the above sub-dosage units, the tablet 10 shown in FIG. 1 and 2 can be severed into dosages of ⅜, ⅝, ¾ or ⅞ of the dosage of the tablet 10 to form the sub-dosage units 90 100 110 120 shown in FIGS. 9–12.

In addition to providing an easily severable tablet 10, the present invention provides the consumer with an accurate determination of how many dosages of the drug have already been taken. Since the amount of remaining sub-dosage units is readily apparent from the face of the tablet 10, the consumer merely has to subtract this number from the total number of sub-dosage units to determine how many dosages of the drug have already been ingested.

Accordingly, the present invention provides a pharmaceutical tablet having multiple score lines, an aperture, and a predetermined dosage which can be easily divided into a plurality of sub-dosage units, each unit having a dosage that is a fraction of the predetermined dosage.

In addition, the present invention provides a tablet having an aperture which reduces the force necessary to sever the tablet and reduces the stress incurred during breakage of the tablet, as compared to the score tablets of the prior art.

Further, the tablet of the present invention provides a plurality of symmetrical score lines on the top surface and the bottom surface of the tablet which reduces the force needed to sever the tablet, as compared to the score tablets of the prior art.

Additionally, the tablet of the present invention can be severed into a plurality of sub-dosage units, each unit having a dosage that is a fraction of the predetermined dosage of the tablet, to accommodate the varying pharmaceutical needs of the consumer.

Likewise, the tablet of the present invention provides an indication of how many dosages of the drug have been previously taken.

Still further, the tablet of the present invention provides a plurality of bevel surfaces that reduce fragmentation of the tablet during severance.

Finally, the tablet of the present invention is generally lower in cost to consumers as compared to the score tablets of the prior art.

While preferred forms and arrangements have been shown in illustrating the invention, it is to be understood that various changes may be made without departing from the spirit and scope of this disclosure.

What is claimed is:

1. A pharmaceutical tablet having a predetermined dosage and a predetermined shape, comprising:

a solid tablet body having an outer periphery, a top surface, a bottom surface, and an aperture extending through said tablet body from said top surface to said bottom surface creating an inner surface of said tablet body, said aperture for reducing the force necessary to sever said tablet, wherein said area of said aperture is at least 15% of said area of said tablet body, and wherein said aperture has a shape that is similar to said predetermined shape of said tablet;

a first bevel edge disposed at the junction of said top surface and said outer surface, a second bevel edge disposed at the junction of said bottom surface and said outer surface, a third bevel edge disposed at the junction of said top surface and said inner surface, and a fourth bevel edge disposed at the junction of said bottom surface and said inner surface, said first, second, third and fourth bevel edges each having angles of inclination of approximately 30° as measured from said top and said bottom surfaces of said tablet; and a first plurality of score lines impressed into said top surface of said tablet body and a second plurality of score lines impressed into said bottom surface of said tablet body, each of said score lines impressed into said top surface lying substantially over a corresponding one of said score lines impressed into said bottom surface, said first and second plurality of score lines extending between said aperture and said outer periphery, said first and second plurality of score lines being V-shaped in cross-section, wherein said first and second plurality of score lines divide said tablet into a plurality of sub-dosage units, each of said plurality of sub-dosage units being of a dosage which is a fraction of said predetermined dosage of said tablet.

2. The pharmaceutical tablet of claim 1, wherein said first plurality of score lines comprises 8 score lines and wherein said second plurality of score lines comprises 8 score lines.

3. The pharmaceutical tablet of claim 1, wherein each of said arms of said first and second plurality of V-shaped score lines are disposed at an angle of approximately 90° from each other.

4. The pharmaceutical tablet of claim 1, wherein each of said plurality of sub-dosage units has identical indicia, whereby each of said plurality of sub-dosage units can be identified from said indicia.

5. A pharmaceutical tablet having a predetermined dosage, comprising:

a solid tablet body with a thickness of approximately 0.230 inches being circular in shape with a diameter of approximately 0.4687 inches and having an outer periphery, a top surface, a bottom surface, and an aperture being circular in shape creating an inner surface of said tablet body, said aperture extending through said tablet body from said top surface to said bottom surface and having a diameter of approximately 0.1875 inches, said aperture for reducing the force necessary to sever said tablet;

a first bevel edge disposed at the junction of said top surface and said outer surface, a second bevel edge disposed at the junction of said bottom surface and said outer surface, a third bevel edge disposed at the junction of said top surface and said inner surface, and a fourth bevel edge disposed at the junction of said bottom surface and said inner surface said first, second, third and fourth bevel edges each having angles of inclination of approximately 30° as measured from said top and said bottom surfaces of said tablet; and at least eight V-shaped score lines impressed into said top surface of said tablet body and at least eight V-shaped score lines impressed into said bottom surface of said tablet body, each of said V-shaped score lines impressed into said top surface lying substantially over a corresponding one of said V-shaped score lines impressed into said bottom surface and each score line having a depth of approximately 0.150 inches and a width of approximately 0.0320 inches, said V-shaped score lines extending between said aperture and said outer periphery, said score lines being V-shaped in cross-section, wherein said V-shaped score lines divide said tablet into at least 8 sub-dosage units, each of said sub-dosage units having a dosage being at least ⅛ of said predetermined dosage of said tablet.

6. The pharmaceutical tablet of claim 5, wherein each of said sub-dosage units has identical indicia, whereby each of said sub-dosage units can be identified from said indicia.

7. The pharmaceutical tablet of claim 5, wherein each of said arms of said V-shaped score lines are disposed at an angle of approximately 90° from each other.

* * * * *